United States Patent [19]

Smith et al.

[11] Patent Number: 4,801,757

[45] Date of Patent: Jan. 31, 1989

[54] NONCRYSTALLINE TRIS(4-HYDROXY-2-METHYL-5-TERT. BUTYLPHENYL) BUTANE

[75] Inventor: Jerry H. Smith; John F. Stephen, both of West Chester, Pa.

[73] Assignee: ICI Americas Inc., Wilmington, Del.

[21] Appl. No.: 125,888

[22] Filed: Nov. 27, 1987

[51] Int. Cl.$^4$ ............................................. C07C 39/16
[52] U.S. Cl. ..................... 568/720; 568/724
[58] Field of Search ............... 568/720, 724, 109, 720, 568/724; 525/109, 194, 192

[56] References Cited

U.S. PATENT DOCUMENTS

| | | | |
|---|---|---|---|
| 3,239,185 | 7/1965 | Ranson | 568/720 |
| 3,239,484 | 3/1966 | Stark | 568/720 |
| 4,319,051 | 3/1982 | Suenobu et al. | 568/720 |
| 4,467,119 | 8/1984 | Thomas | 568/724 |

FOREIGN PATENT DOCUMENTS

| | | | |
|---|---|---|---|
| 949940 | 2/1964 | United Kingdom | 568/720 |
| 951935 | 3/1964 | United Kingdom | 568/720 |

OTHER PUBLICATIONS

Kahovec et al, "Coll. Czech. Chem. Comm" vol. 33 (1969), pp. 1709-1729.

*Primary Examiner*—Werren B. Lone

[57] ABSTRACT

A noncrystalline 1,1,3-tris(2-methyl-4-hydroxy-5-tert-butylphenyl)butane having an amorphous X-ray defraction pattern and a melt transition temperature of 113°–119° C. is made by an improved process and offers improvements over crystalline materials as a stabilizer of resins made from at least one ethylenically unsaturated monomer such as polypropylene.

7 Claims, No Drawings

NONCRYSTALLINE TRIS(4-HYDROXY-2-METHYL-5-TERT. BUTYLPHENYL) BUTANE

The invention relates to 1,1,3 tris(4-hydroxy-2-methyl-5-tert.butylphenyl) butane in a noncrystalline solvent-free anhydrous form and a process for its manufacture. The novel product shows improved antioxidant and blending characteristics when employed as an additive for polyolefins such as polypropylene.

Crystalline forms of tris(4-hydroxy-2-methyl-5-tert-butylphenyl) butane for use as antioxidants were first described in U.S. Pat. No. 3,196,185. An improved process for manufacture of these crystalline products has been recently described in U.S. Pat. No. 4,467,119. A U.S. Pat. No. 4,319,051 describes a crystalline trihydrate of the same compound. It has been found that a more useful form of the subject compound can be made in the form of an amorphous powder. This new form is free of volatile materials, free of water of hydration, free of flammable solvents, has a higher active content and can be more efficiently blended with polymeric materials.

Surprisingly, the product of the invention is made by an expedient variation of previously described processes. The product is made according to the following simplified process:

(a) A molor quantity of crotonaldehyde is condensed with a three-molar portion of 3-methyl-6-tert.butyl-phenol (TBMC) in a solvent such as methanol in the presence of aqueous acid at temperatures of 50°–100° C.

(b) The hot mix is quenched with a solution of aqueous base to neutralize the solution to a pH of 6–7.

(c) The aqueous slurry resulting is then cooled to room temperature and filtered to collect solid product.

(d) The solid product is washed with aqueous solvent until all color is removed.

(e) The filter cake may be further washed with pure water to remove residual solvent.

(f) The filtrate is dried under vacuum at 50°–59° C. to produce an amorphous, anhydrous product.

The amorphous compound provided by the invention is a more efficient antioxidant in that it is usually added to high molecular weight hydrocarbons such as natural and synthetic rubber, polyolefins, polyester and particular polyethylene, polypropylene and polyethylene terephthalates. The product blends with these resin compositions in a more satisfactory manner in that it is free of moisture and volatile solvent.

The product of the invention is characterized as being free of crystallinity or amorphous as determined by X-ray defraction, and has a melting transition point in a range of 113°–119° C. as determined by the differential scanning calorimeter technique (DSC V2.2A DuPont 9900) when heated in nitrogen at 10° C. per minute. When subject to nuclear magnetic resin anaylsis (NMR) for carbon 13 and proton shift, the spectra are indicated in Tables I and II respectively.

TABLE I

| Peak # | (PPM) | Peak # | (PPM) |
|---|---|---|---|
| 1 | 153.0 | 15 | 117.9 |
| 2 | 152.9 | 16 | 117.5 |
| 3 | 133.8 | 17 | 117.3 |
| 4 | 133.7 | 18 | 44.9 |
| 5 | 133.1 | 19 | 38.0 |
| 6 | 132.9 | 20 | 34.0 |
| 7 | 132.6 | 21 | 34.0 |
| 8 | 132.3 | 22 | 31.1 |
| 9 | 132.1 | 23 | 29.6 |
| 10 | 132.0 | 24 | 29.4 |
| 11 | 131.2 | 25 | 29.3 |
| 12 | 125.2 | 26 | 22.6 |
| 13 | 124.9 | 27 | 18.2 |
| 14 | 123.0 | 28 | 17.6 |

TABLE II

| CHEMICAL SHIFT (PPM) | ASSIGNMENT |
|---|---|
| 8.89, 8.90, 8.91 | 3 singlets, 3H, phenolic-OH |
| 6.42, 6.46, 6.48, 6.90, 6.99, 7.20 | all singlets, 6H, aromatic H |
| 3.70 | multiplet, 1H, aliphatic CH |
| 2.77 | multiplet, 1H, aliphatic CH |
| 1.50, 1.63, 2.02 | 3 singlets, 9H, aromatic-METHYLS |
| 1.92 | multiplet, 2H, aliphatic CH2 |
| 1.21, 1.34, 1.36 | 3 singlets, 27H, t-butyls |
| 1.10 | doublet, 3H, aliphatic CH3 |

Dimethyl sulfoxide was used as the NMR solvent. Tetramethylsilane (TMS) was used as an internal reference (set to 0ppm).

The process of the invention can be better understood by referring to the following nonlimiting examples wherein all proportions are expressed in parts by weight unless otherwise specified.

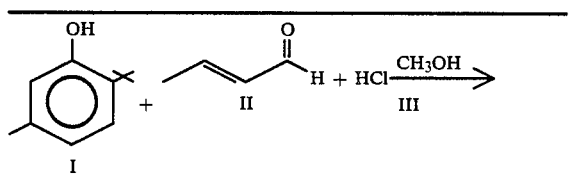

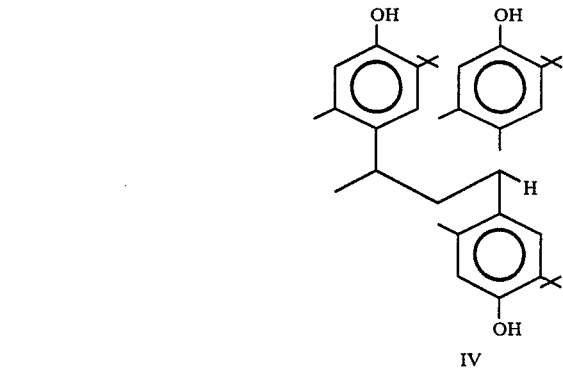

| Material | MW | Moles | Amt. Used |
|---|---|---|---|
| I. TBMC | 164.25 | 3.09 | 506.8 g |
| II. Crotonaldehyde | 70.09 | 1.00 | 70.0 g |
| III. HCl (36%) aqueous | 36.47 | 1.12 | 96.6 ml |

PROCESS

A 3-1, 3-neck, round bottom flask was equipped with a mechanical stirrer, and addition funnel, a cold water condenser, a thermometer, and a stopper. The flask was heated with a thermostated heating mantle.

Reactants I and III were combined in the reaction flask with 380 ml methanol and heated to 75° C. with stirring. Reactant II was added slowly over a period of 30 minutes. The reaction was exothermic, causing the reaction mixture to reflux. After a few minutes, a solid appeared and the reaction mixture became thicker as the reaction proceeded. The reaction was allowed to progress for 1 hour after addition of II. The improved process is demonstrated in the following recovery procedures:

EXAMPLE 1

The reaction product was quenched, while hot (50°–80° C.), by addition of 165 ml of methanol and 265 ml of 2M $Na_2CO_3$ solution. The purpose of the added methanol is to provide a workable slurry consistency of the reaction mixture for filtration. The pH of the reaction mixture was checked to insure complete neutralization (pH=6–7). An Additional few ml $Na_2CO_3$ solution was occasionally needed.

The reaction mixture was cooled and filtered through a medium-frit funnel. The filter cake was washed with 80% aqueous methanol until all color was removed (typically 1100 ml) followed by 500 ml water. The wet filter cake containing 25–40% water was dried under vacuum (50mm) at 50°–90° C. to give anhydrous (<1% water) white solid.

EXAMPLE 2

The reaction was quenched, while hot (50°–80° C.), by addition of 265 ml of water and 265 ml of 2M $Na_2CO_3$ solution to provide a workable consistency for filtration. The pH of the reaction mixture was checked to insure complete neutralization (pH=6–7). An additional few ml $Na_2CO_3$ solution was occasionally needed.

The reaction mixture was cooled and filtered through a medium-frit funnel. The filter cake was washed with 500 ml water to remove salts followed by 80% aqueous methanol until all color was removed (typically 1500 ml). The wet filter cake containing 25–40% solvent was dried under vacuum (50mm) at 50°–90° C. to give anhydrous white solid.

The products obtained by Examples 1 and 2 procedures typically contain less than 1% water and analyzed greater than 96% pure. The melting transition range was usually about 113°–119° C. Yeilds were about 80% based on crotonaldehyde.

Equivalent aqueous acids for use in the process include sulfuric acid, p-toluene sulfonic acid, and methane sulfonic acid.

Equivalent aqueous bases for use in the process include potassium carbonate, sodium hydroxide, and potassium hydroxide.

Equivalent aqueous solvents for use in the washing process include ethanol and i-propanol.

The noncrystalline product of this invention is used as a stabilizer for organic material normally subject to thermal and oxidative deterioration. Materials which are thus stabilized include synthetic organic polymeric substances such as vinyl resins formed by the polymerization of ethylenically unsaturated monomers such as vinyl halides or from the copolymerization of vinyl halides with unsaturated polymerizable compounds for example vinylesters, α, β-unsaturated ketones, α, β-unsaturated aldehydes and unsaturated hydrocarbons such as butadienes and styrenes; poly-α-olefins, such as polyethlene, polypropylene, polybutylene and the like including copolymers of poly-α-olefins, polyurethanes and polyamides such as polyhexamethylene adipamide and polycaprolactum; polyesters such as polyethylene terephthalates; polycarbonates, polyacetals, polystyrene; polyethyleneoxide; polyisoprene; polybutadiene and copolymers such as those of high impact polystyrene containing copolymers of butadiene and styrene and those formed by the copolymerization of acrylonitrile, butadiene and/or styrene.

In general, the material of the invention is used in amounts of about 0.005–5% by weight of the organic material to be stabilized. The material is used advantageously in a range of from about 0.05% to about 2% by weight. It is particularly effective in stabilizing polyolefins such as polyethylene and polypropylene.

The material of the invention is incorporated in a polymeric substance during the usual processing operations for example, by milling, or extrusion. The stabilized polymer can be fabricated into films, fibers, filaments, halospheres and the like. The heat stabilizing properties of the material are used to stabilize the polymer against degradation during such processing at high temperatures generally encountered. The noncrystalline product of the invention can also be used in combination with other stabilizers or additives. Especially useful costabilizers are dilauryl-β-thiodipropionate and distearyl-β-thiodipropionate (DSTDP). Additional costabilizers include di- and tri-alkyl and alkylphenyl phosphites such as tris-nonylphenyl phosphite, tris ditertbutylphenyl phosphite, bis(2,4-t-butylphenyl) pentaerythritol diphosphite, tetra(di-tert-butylphenyl) diphenyl-4,4'-ene-diphosphonite, and distearyl pentaerythritol diphosphite.

Other antioxidants, antiozonants, thermal stabilizers, ultraviolet light absorbers, coloring etc., may also be used in the composition in combination with the stabilizers of this invention.

EXAMPLES 3–7

In order to illustrate the effectiveness of the noncrystalline product of the invention as a resin stabilizer, the noncrystalline material of Example 1 was incorporated with polypropylene resin (PROFAX 6301, a product of Himont Corporation)by solvent blending (methylene chloride) at concentrations of 0.1% by weight of the total resin and in some instances was coblended with 0.25% DSTDP costabilizer.

The resin was extruded using a Brabender extruder with conditions as follows: Zone 1, 200° C.; Zone 2, 215° C.; and Zone 3, 230°–° C.; a 4:1 screw was utilized and the screw speed was 60 rpm. The pelletized resin from each formulation was compression molded at 6,000 psi at 188° C. to form 25 mil test plaques.

For comparison, formulations were prepared by incorporating a commercially available, crystalline, solvent-free sample of tris(4-hydroxy-2-methyl-5-tert-butylphenyl) butane and were subjected to the test procedures.

OVEN AGING TEST COLOR DEVELOPMENT—TABLE III

Color development at 150° C. for each formulation was monitored by utilizing a Gardner colorimeter to measure plaque yellowness index values. Readings were taken initially and at 100 hour intervals for 500 hours.

In general, the noncrystalline product of Example 1 is equivalent to the commercially prepared crystalline material in the prevention of color formation upon aging.

OVEN AGING EMBRITTLEMENT TIMES—TABLE IV

Compression molded 25 mil plaques from each formulation were oven aged at 150° C. until embrittlement.

In general, the perforamnce of the noncrystalline product of Example 1 is equivalent to the commercial, crystalline product. It outperforms the crystalline product when used in combination with the costabilizer such as DSTDP.

MELT FLOW AND COLOR UPON MULTIPLE EXTRUSIONS—TABLES V AND VI

The formulations were evaluated for both melt flow and color stability upon multiple extrusions. For melt stability testing, a Tinius Olson melt flow indicator was used to evaluate the resins at 230° C. with a 2.16 kilogram weight. Color was measured with a Gardner Colorimeter.

In general, both the melt flow and color stability performance of the noncrystalline product of Example 1 are equivalent to the crystalline material.

TABLE III

| | | Oven Aging Test Color Development | | | | | |
|---|---|---|---|---|---|---|---|
| Ex | | Concentration | Time (hrs) Yellowness Index at 150° C. | | | | |
| No | Additive | (wt %) | 0 | 100 | 200 | 400 | 500 |
| 3 | Control | | 5.8 | — | — | — | — |
| 4 | Ex 1 | 0.1 | 8.6 | 36.8 | 43.0 | — | — |
| 5 | Commercial Crystals | 0.1 | 9.3 | 35.3 | 40.7 | — | — |
| 6 | Ex 1/DSTDP | 0.1/0.25 | 6.8 | 20.5 | 25.0 | 32.3 | 34.6 |
| 7 | Commercial Crystals/DSTDP | 0.1/0.25 | 6.9 | 20.6 | 24.1 | 33.1 | 35.3 |

TABLE IV

| | | Oven Aging Embrittlement Time | |
|---|---|---|---|
| Ex | | Concentration | Embrittlement Time |
| No | Additive | (wt %) | (hrs at 150° C.) |
| 3 | Control | | 24 |
| 4 | Ex 1 | 0.1 | 72 |
| 5 | Commercial Crystals | 0.1 | 72 |
| 6 | Ex 1/DSTDP | 0.1/0.25 | 942 |
| 7 | Commercial Crystals/DSTDP | 0.1/0.25 | 864 |

TABLE V

| | | Melt Flow Index Value After Multiple Extrusion | | | | | |
|---|---|---|---|---|---|---|---|
| Ex | | Concentration | M/F Index Value g/10 Min. (Extrusion No.) | | | | |
| No | Additive | | 1 | 2 | 3 | 4 | 5 |
| 6 | Ex 1/DSTDP | 0.1/0.25 | 10.3 | 11.5 | 11.0 | 12.0 | 13.9 |
| 7 | Commercial Crystals/DSTDP | 0.1/0.25 | 10.2 | 11.7 | 12.0 | 11.5 | 13.3 |

TABLE VI

| | | Color Development After Multiple Extrusion | | | | | |
|---|---|---|---|---|---|---|---|
| Ex | | Concentration | Yellowness Index (Extrusion No) | | | | |
| No | Additive | (wt %) | 1 | 2 | 3 | 4 | 5 |
| 6 | Ex 1/DSTDP | 0.1/0.25 | 6.6 | 7.2 | 7.7 | 8.2 | 9.1 |
| 7 | Commercial Crystals/DSTDP | 0.1/0.25 | 6.9 | 7.4 | 7.8 | 8.5 | 8.9 |

What is claimed is:

1. A noncrystalline 1,1,3-tris(2-methyl-4-hydroxy-5-tert-butylphenyl) butane having an amorphous X-ray defraction pattern and characterized by a melt transition temperature of 113°–119° C. as determined by differential scanning calorimetry.

2. A process for the manufacture of a composition of claim 1 which comprises the steps of
   (a) reacting a molar portion of crotonaldehyde with a three molar portion of 3-methyl-6-tert-butylphenol in an alcohol solution in the presence of aqueous acid at a temperature of 50°–100° to form a hot precipitate mix, and
   (b) quenching said hot precipitate mix reaction product with aqueous base to neutralize said acid to a pH of 6–7 to cool to room temperature, and
   (c) removing said precipitate by filtration and thereafter washing with aqueous solvent to remove starting materials and by-products.

3. A process according to claim 2 where the alcoholic solvent is methanol.

4. A process according to claim 2 where the aqueous wash solvent is aqueous methanol.

5. A composition comprising a polymerized ethylenically unsaturated monomer and 0.005–5% by weight of the material of claim 1.

6. A composition of claim 5 comprising a resin selected from the group consisting of polyethylene, polypropylene and polystyrene.

7. A composition of claim 6 further comprising a costabilizer compound selected from the group consisting of dilauryl-β-thiodipropionate, distearyl-β-thiodipropionate, distearylpentaerythritol diphosphite, pentaerythritol tetrakis 3-(dodecylthio)-propionate, tris(2,4-di-tert-butylphenyl) phosphite, bis(2,4-di-tert-butylphenyl)pentaerythritol di phosphite, and tetrakis(2,4-di-tert-butylphenyl)diphenyl-4,4'-ene-diphosphonite.

* * * * *